(12) United States Patent
Lu et al.

(10) Patent No.: US 7,290,723 B1
(45) Date of Patent: Nov. 6, 2007

(54) AEROSOL SPLITTER FOR ELSD

(76) Inventors: Jiang Lu, 514 Briggs Pl., Superior, CO (US) 80027; Samuel Frederick Azlein, 14688 Madison St., Brighton, CO (US) 80602

( * ) Notice: Subject to any disclaimer, the term of this patent is extended or adjusted under 35 U.S.C. 154(b) by 517 days.

(21) Appl. No.: 10/784,497

(22) Filed: Feb. 23, 2004

Related U.S. Application Data

(60) Provisional application No. 60/457,637, filed on Mar. 26, 2003.

(51) Int. Cl.
*B05B 1/24* (2006.01)
*B05B 7/16* (2006.01)
*B05B 1/26* (2006.01)
*B05B 1/00* (2006.01)
*A62C 31/02* (2006.01)

(52) U.S. Cl. .............. 239/135; 239/132.3; 239/128; 239/461; 239/589; 239/597; 239/265.19; 239/124

(58) Field of Classification Search ............ 239/135, 239/132.3, 128, 461, 589, 597, 265.19, 124
See application file for complete search history.

(56) References Cited

U.S. PATENT DOCUMENTS

| | | | | |
|---|---|---|---|---|
| 3,341,080 A | * | 9/1967 | Wittke | 222/146.3 |
| 4,917,830 A | * | 4/1990 | Ortiz et al. | 261/18.1 |
| 5,922,947 A | * | 7/1999 | Hobbins | 73/64.56 |
| 6,122,055 A | | 9/2000 | O'Donohue et al. | |
| 6,151,113 A | | 11/2000 | O'Donohue et al. | |
| 6,229,605 B1 | | 5/2001 | Benedict | |
| 6,362,880 B1 | | 3/2002 | Anderson, Jr. et al. | |
| 6,485,689 B1 | * | 11/2002 | Huang et al. | 422/83 |
| 6,528,018 B1 | * | 3/2003 | Berndt | 422/70 |

OTHER PUBLICATIONS

Alltech Model 500 ELSD Operating Manual, Sep. 1996, pp. 3, 15.
Sedex 55 ELSD Instruction Manual, 1984?, pp. 7, 15, 17,24.
Sales of ELSD instruments by SofTA Corporation (Inga Henderson, V.P.).
Pittcon announcement of SofTA ELSD on Mar. 10, 2004 (Chicago, IL).

* cited by examiner

*Primary Examiner*—Davis Hwu

(57) ABSTRACT

The present invention is directed to a device for splitting a propelled aerosol cloud. The device utilizes a curved spray chamber and a thermal technique to divert any desired portion of the aerosol to waste. The remainder of the aerosol is made available to an ELSD or similar instrument for analysis.

4 Claims, 6 Drawing Sheets

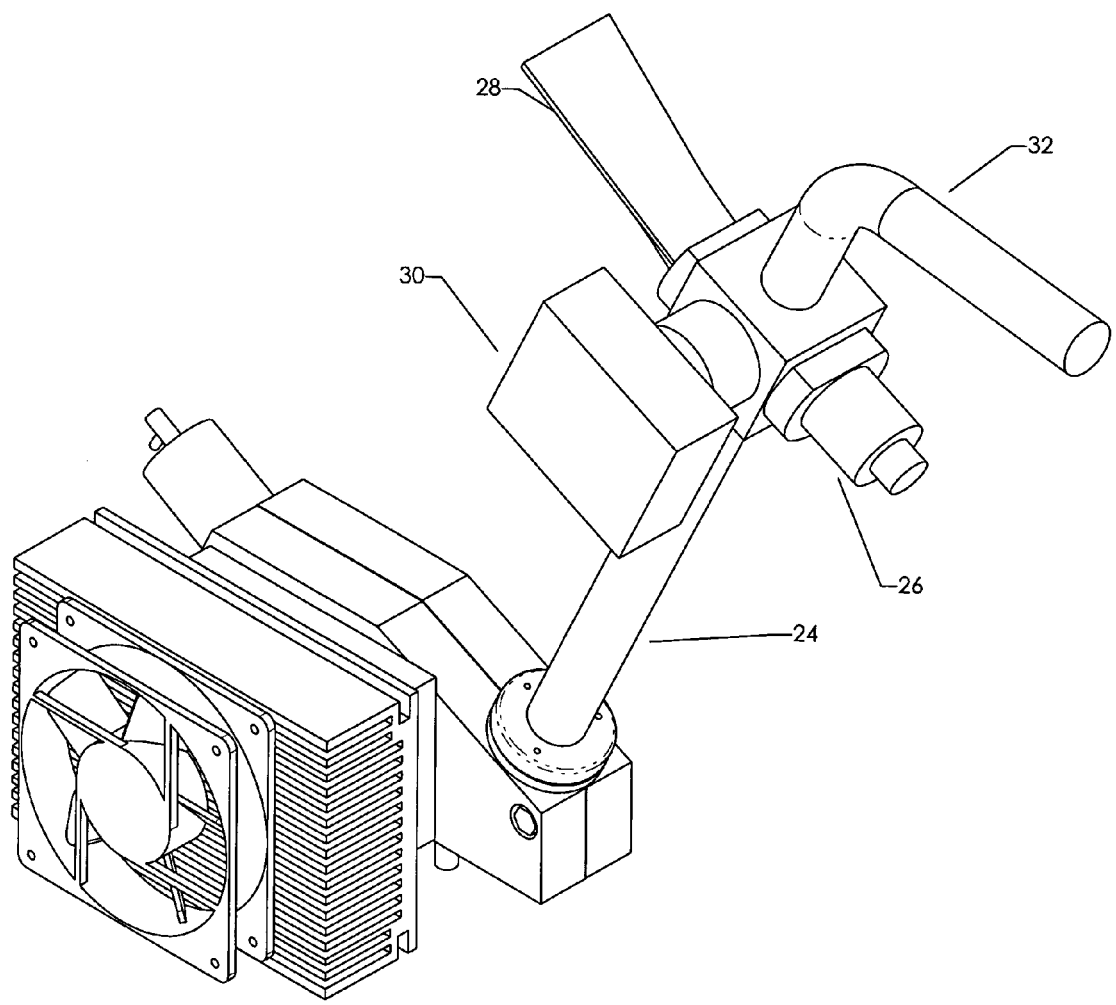
Figue 5

AEROSOL SPLITTER FOR ELSD

CROSS-REFERENCE TO RELATED APPLICATIONS

Provisional Patent Application No. 60/457,637 filed on Mar. 26, 2003

FEDERALLY SPONSORED RESEARCH

Not Applicable

SEQUENCE LISTING OR PROGRAM

Not Applicable

BACKGROUND OF THE INVENTION

1. Field of Invention

This invention relates to division of an aerosol cloud formed by a nebulizer within an Evaporative Light Scattering Detector.

2. Background of the Invention

An Evaporative Light Scattering Detector (ELSD) is an analytical instrument for detecting and quantifying samples that have been separated by any of a variety of chromatographic methods. Such methods include but are not limited to High Performance Liquid Chromatography (HPLC), Supercritical Fluid Chromatography (SFC), and Gel Permeation Chromatography (GPC).

The simplest embodiment of an ELSD has a nebulizer, a heated zone or drift tube, a light source, and an amplifier, which converts scattered light into an electrical signal. In operation, the column effluent, which contains both the mobile phase and analyte, is first sent to the nebulizer. The nebulizer transforms the effluent into an aerosol cloud, and propels the cloud into the instrument. As the aerosol cloud enters the drift tube, which is heated, the more volatile mobile phase evaporates, leaving a cloud of analyte particles. These particles scatter light from the light source. The scattered light is amplified by a photo-multiplier tube, photo-diode, or similar device into a useable electrical signal.

This simplest embodiment, referred to as "full flow" in U.S. Pat. No. 6,629,605 and illustrated as FIG. 1 in same, has many limitations. Principally, it will only evaporate modest amounts of volatile mobile phases. While limited, full flow instruments are quite sensitive within their permissible operating range. The ALLTECH MODEL 500 is an example of such an instrument. To address the problem of limited evaporative power, several solutions have been tried.

One solution, available on instruments form SEDERE involves a nebulization chamber (spray chamber) placed between the nebulizer and drift tube. The nebulized effluent is divided in this chamber by impaction/condensation on the walls of the chamber. The chamber is geometrically constructed such that larger aerosol droplets hit the wall and run out a drain, while smaller aerosol droplets follow gas flow through the spray chamber and enter the drift tube. U.S. Pat. No. 6,229,605 refers to these instruments as "split-flow" designs. As pointed out in the above-cited patent, split-flow instruments accommodate high effluent flow rates and difficult to evaporate mobile phases, but they do not always pass on enough aerosol to maximize sensitivity.

A second solution is available from ALLTECH ASSOCIATES, as a MODEL 2000. This instrument has a splitter that can be turned on or off, as described in the above-cited patent. Turning the splitter on involves rotating a plate impactor perpendicular to aerosol flow. Large aerosol droplets hit the plate, condense, and exit a drain. Smaller aerosol droplets traverse the annular space between impactor and wall, and continue on to the drift tube. Turning the impactor plate parallel to the aerosol flow essentially removes it from the instrument, which then becomes "full flow". Thus the instrument is easily converted from "split-flow" to "full flow" modes.

The above-described design has advantage over earlier art, but still has objectionable limitations. Namely, (1) it has no intermediate settings, and (2) it relies on mechanical means (motor, solenoid or the like) to move the impactor.

As a detector for chromatography, an ELSD may reasonably be expected to handle a wide variety of effluent flow rates and mobile phase compositions. An on/off design, as described in U.S. Pat. No. 6,229,605, handles the extremes adequately, but cannot be optimized for moderate flow rates, or moderately difficult to evaporate mobile phases. Also, motors, solenoids, shaft seals and linkages are possible sources of mechanical failure.

OBJECTS AND ADVANTAGES

As can be seen from the above discussion, the prior art of aerosol splitters does not meet the needs of an ELSD user.

Several objects and advantages of the present invention are:

(a) to provide an aerosol splitter that is smoothly variable over a wide dynamic range. This allows an ELSD to be optimized for the wide variety of conditions encountered in chromatography.

(b) to provide an aerosol splitter without complex mechanical components.

(c) to provide an aerosol splitter whose variable split ratio is under user control.

(d) to provide an aerosol splitter capable of smoothly changing during a gradient run in chromatography. Gradient separations use more than one solvent in time-programmed compositions. Each composition requires a unique setting for the best instrument sensitivity.

Still further objects and advantages will become apparent from a consideration of the ensuing description and drawings.

SUMMARY

The present invention utilizes a combination of geometry and thermal technique to split an aerosol cloud. A user, by changing only one temperature, can vary the split over a wide dynamic range.

DRAWINGS—FIGURES

FIG. 5 shows the splitter assembled in a typical ELSD configuration.

DRAWINGS—Reference Numerals

12 Nebulizer
14 Nebulizer Holder
16 Spray Chamber
16a Straight Section
16b Curved Section
16c Drain
18 Clamshell, left
20 Clamshell, right
22 Thermoelectric Plate
22a Heat Sink
23 Fan
24 Drift Tube
26 Light Source
28 Light Trap
32 Exhaust Tube

DETAILED DESCRIPTION—PREFERRED EMBODIMENT

Figure 1:
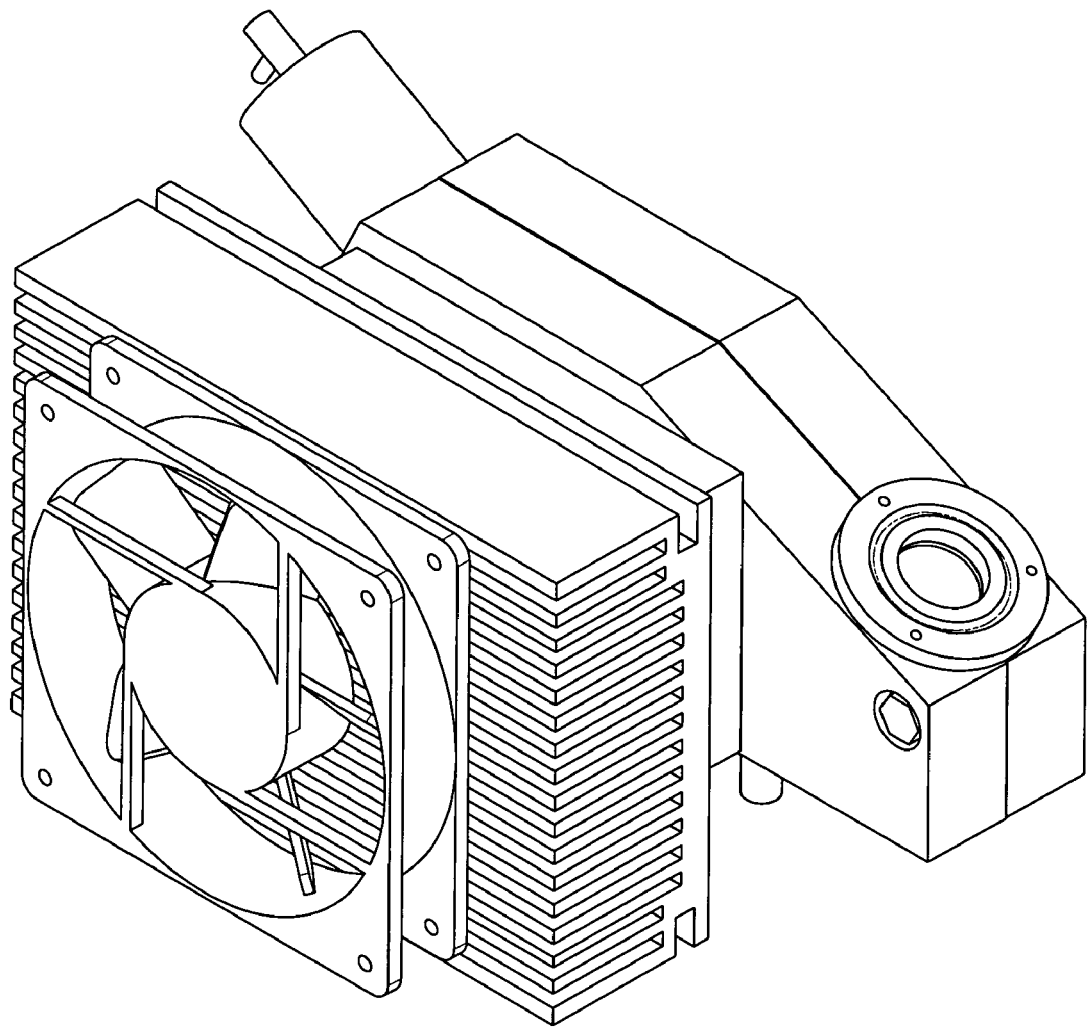
FIG. 1 shows the splitter assembled, and in perspective view.
Figure 2A:
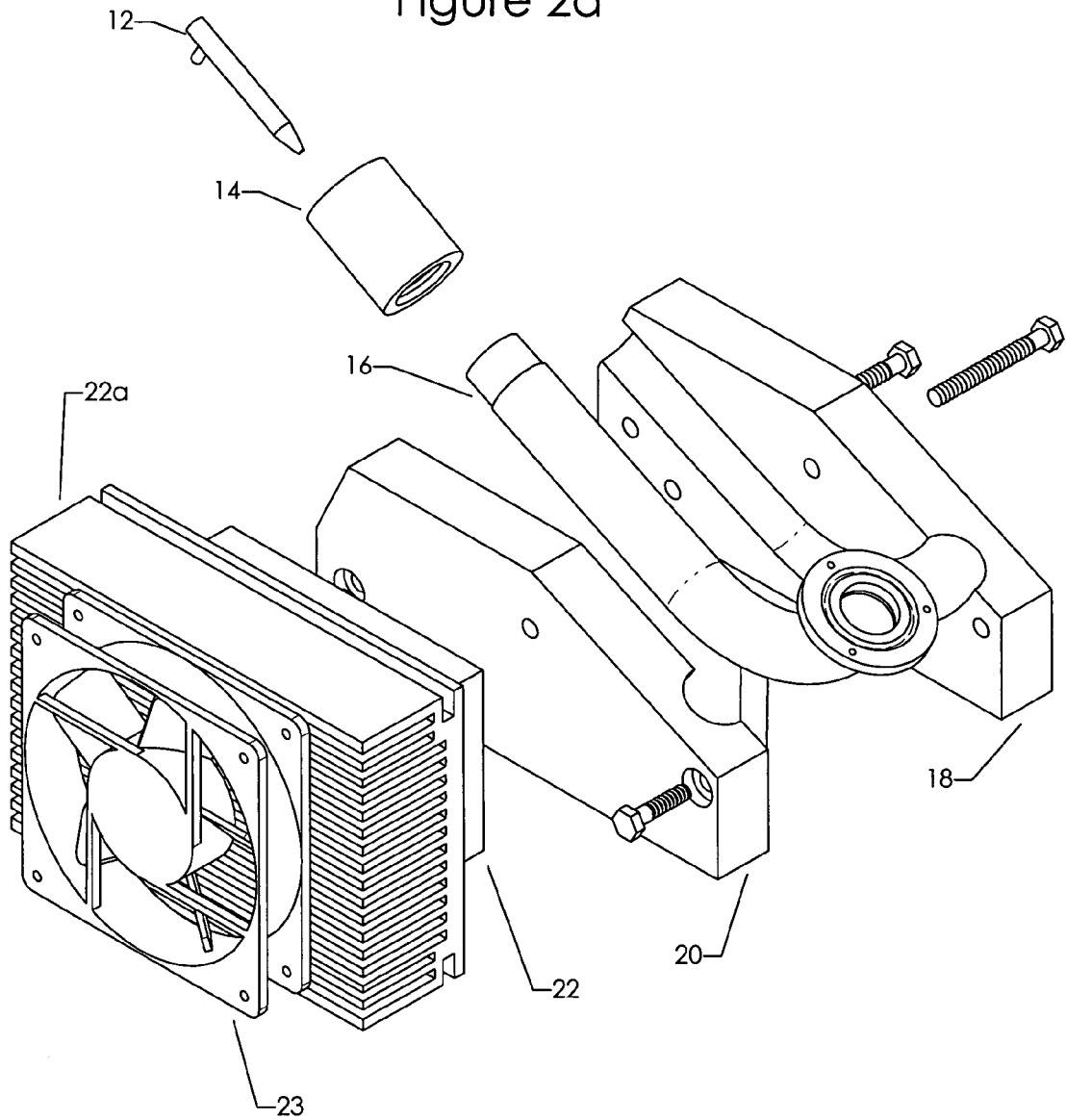
FIGS. 2a and 2b show exploded views of the splitter, illustrating how parts interact.
Figure 2B:
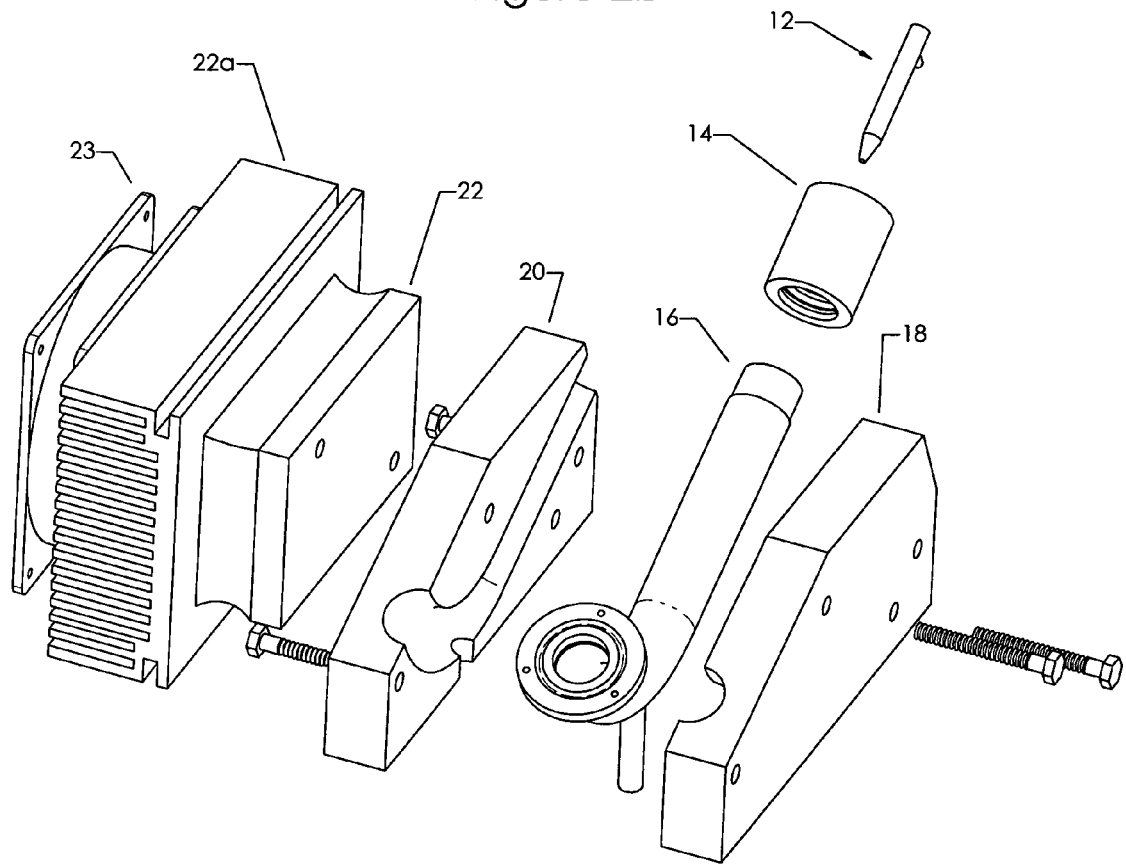
Figure 3A:
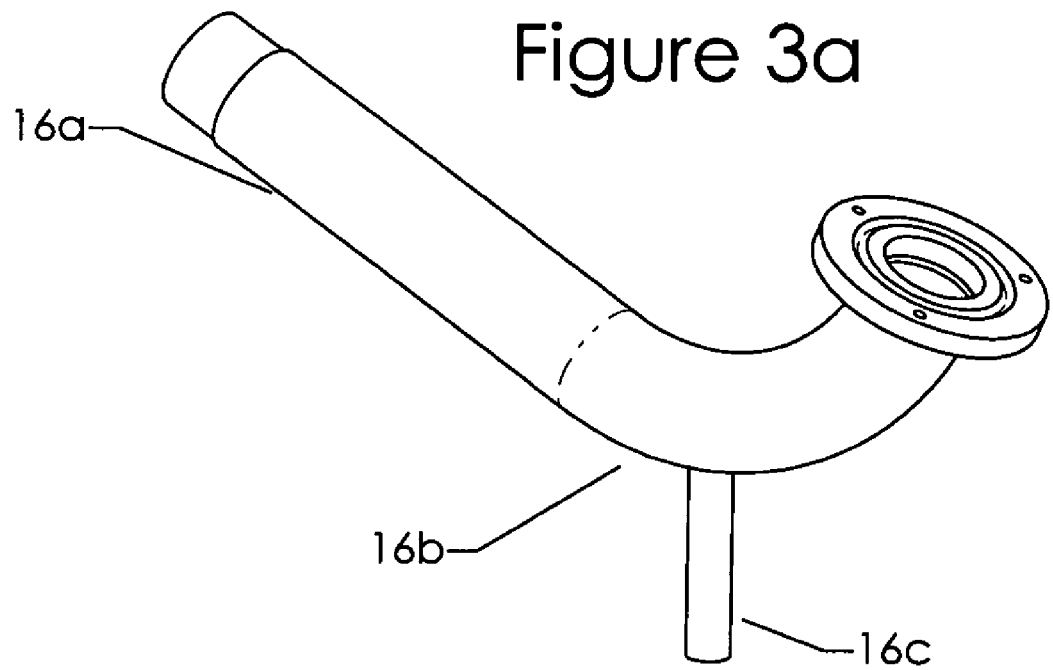
FIGS. 3a and 3b show the spray chamber in perspective and in cut-away.
Figure 3B:
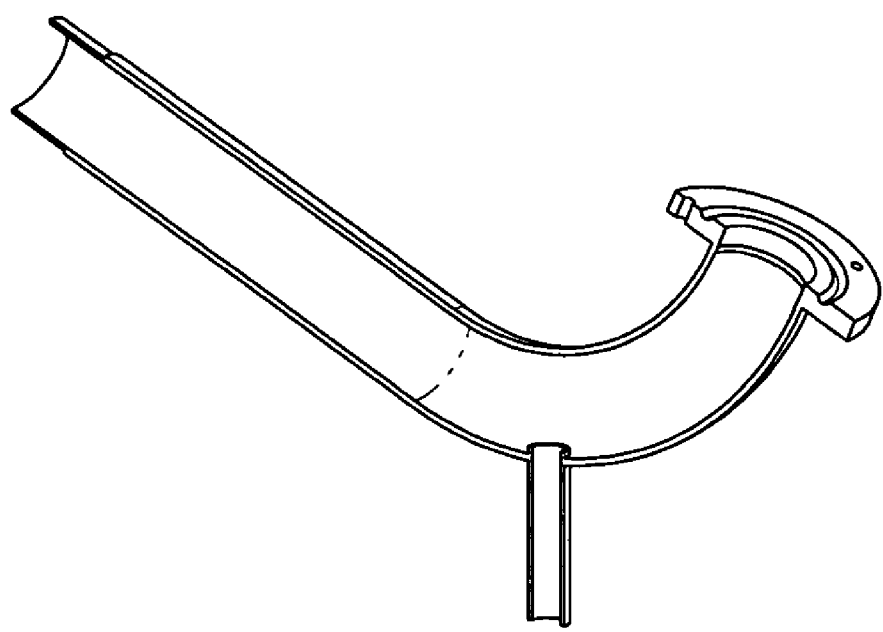
Figure 4A:
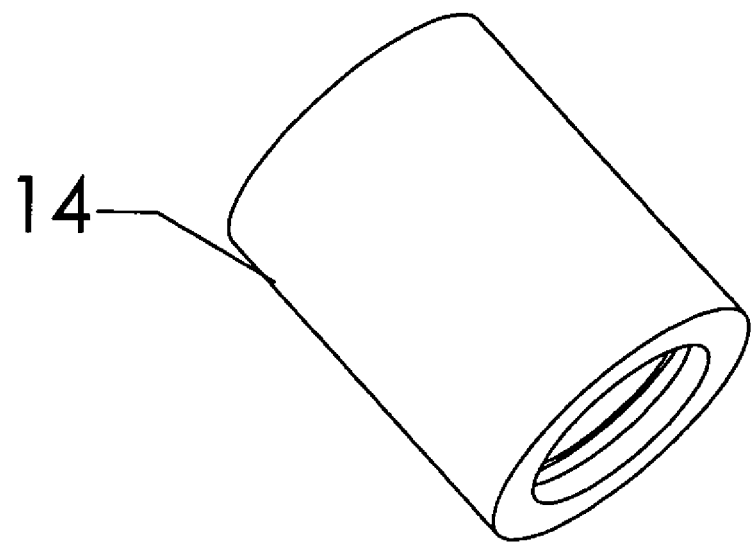
FIGS. 4a and 4b shows the nebulizer holder in perspective and in cut-away.
Figure 4B:
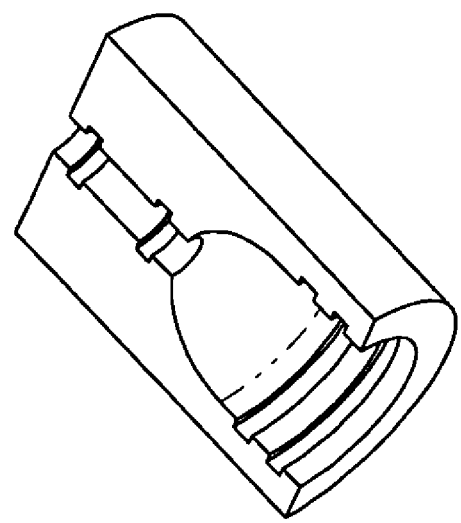

With principal reference to FIG. 2a, a preferred embodiment of the aerosol splitter is illustrated. The device comprises a nebulizer 12. The nebulizer is preferably an Elemental Scientific, Inc. model PFA-LC-2. The nebulizer 12 inserts into a Nebulizer Holder 14. The Nebulizer Holder 14 makes a gas tight connection between the Nebulizer 12 and the Spray Chamber 16. FIGS. 4a and 4b show the Nebulizer Holder in greater detail. FIG. 4b shows the grooves, which hold O-rings. These O-rings (not shown) make gas tight seals around both Nebulizer 12 and Spray Chamber 16.

The Spray Chamber 16 ultimately attaches to a Drift Tube 24 within the completed instrument, as illustrated in FIG. 5. To facilitate the attachment, the Spray Chamber 16 has a groove in the flange, which accommodates an O-ring (not shown). The O-ring allows for a gas tight connection while providing a measure of thermal isolation. Thermal isolation allows the Spray Chamber 16 and Drift Tube 24 to operate at different temperatures.

The Spray Chamber 16 is preferably constructed from 316 stainless steel, providing both good resistance to corrosion and good heat transfer. The Spray Chamber 16 is firmly sandwiched between two Clamshells 18 and 20. These Clamshells 18 and 20 have a cavity milled within that matches the configuration of the Spray Chamber 16. Firmly connected to the right Clamshell 20 is a Thermoelectric Plate (also known as a peltier device) 22. The Thermoelectric Plate 22 is preferably a TE Technology, Inc. Model CP-2721. Depending on the polarity of Direct Current (DC) electricity supplied to the Thermoelectric Plate 22, and in the presence of sufficient airflow across the Heat Sink 22a of the Thermoelectric Plate 22, said Thermoelectric Plate 22 will become either a heater or a cooler. An electric Fan 23 supplies sufficient airflow in this embodiment. In turn, the Thermoelectric Plate 22 will heat or cool the clamshells 18 and 20 and the Spray Chamber 16 located within them.

As illustrated in FIGS. 3 and **3*a*, the Spray Chamber 16 has a Straight Section 16*a*. The Straight Section 16*a* is followed by a Curved Section 16*b*. When oriented as shown in FIG. 3, the Curved Section 16*b* has a Drain 16*c*** located at its lowest point.

When particles exit the nebulizer at a high velocity, they have a momentum based on that velocity and upon their mass. Given the same velocity, larger particles will have more momentum than smaller particles. Above a critical momentum value, a particle will impact the wall of the Curved Section **16*b*. Below this value the particle will follow gas flow around the Curved Section 16*b* and enter the Drift Tube 24**.

When the Thermoelectric Plate 22 is in cooling (sub-ambient) mode, the spray Chamber 16 is also cooled due to its intimate mechanical contact. A cool Spray Chamber 16 will tend to condense the aerosol droplets exiting the nebulizer. These new larger droplets will tend to have their momentum carry them into Curved Section **16*b*. They then condense and exit the Drain 16*c***.

When the Thermoelectric Plate 22 is in heating mode, the Spray Chamber 16 is also heated due to its intimate mechanical contact. A heated Spray Chamber 16 will partially evaporate the aerosol droplets exiting the nebulizer. These new smaller droplets will tend to be carried around the Curved Section **16*c* by the airflow, where they will enter the Drift Tube 24**.

After evaporation in the Drift Tube 24, the analyte particles pass in front of light emitted from Light Source 26. Most of the emitted light passes through and is trapped by Light Trap 28, however the analyte will scatter some of the incident light. The scattered light is detected and amplified by Amplifier 30. Evaporated mobile phase and analyte exit via Exhaust Tube 32.

The most preferred embodiment of the present invention may have the following dimensions for the Spray Chamber 16.

Outer Diameter 1" with a small section at the straight end reduced to 0.95"

Inner Diameter 0.85"

Curved Section 90 degree arc, with radius of 2.5" at center.

Straight Section 4.5"

OPERATION

From the above discussion it can be appreciated by those skilled in the art that a curved Spray Chamber 16 can act as a controllable aerosol splitter when its walls undergo controlled temperature excursions. The splitting can be varied over a wide range by changing only one temperature. This invention places smoothly variable split ratios under operator control, without the use of complex mechanical mechanisms.

To use the splitter, the ELSD into which it is built will have both a temperature display with a user definable set point, and appropriate Thermoelectric Plate 22 drive circuitry. When a set point is entered above the present temperature of the Spray Chamber 16, the drive circuitry will power the Thermoelectric Plate 22 in such a way that it is a heater. Conversely, when the set point is below the present temperature of the Spray Chamber 16, the drive circuitry will power the Thermoelectric Plate 22 in such a manner that it is a cooler.

The user may decide whether to send more or less aerosol to the Drift Tube 24 by monitoring the baseline of the instrument for a given Drift Tube 24 temperature. Temperature of the Spray Chamber 16 can be increased until it is no longer possible for the Drift Tube 24 to successfully evaporate the aerosol, resulting in a noisy baseline. Reducing the Spray Chamber 16 temperature slightly from this point gives greatest instrument sensitivity.

In operation, the illustrated Spray Chamber 16 can divert from 1% to 99% of many mobile phases to drain, when operated between 80° C., and 0° C. This has been shown to be sufficient for a wide range of effluents and flow rates.

CONCLUSIONS, RAMIFICATIONS AND SCOPE OF INVENTION

The reader can see that the invention provides a way of optimizing the aerosol split ratio of an ELSD for maximum instrument response, and for a wide variety of mobile phase types and flow rates. Previous art has either not allowed the split ratio to be varied under user control, or has provided only extreme settings.

While the above description contains many specificities, these should not be construed as limitations on the scope of the invention, but rather as an example of one preferred embodiment. Without departing from the invention, many other variations are possible.

For example, the Nebulizer Holder 14 may have many different constructions. It could have threaded portions that compress O-rings, instead of static seals. The overall shape of the inner chamber could also be modified without departure from the invention.

The Nebulizer 12 could be of many different types. The illustrated type is a concentric flow pneumatic nebulizer, but cross flow, non-concentric, and ultrasonic could all be employed.

The Spray Chamber 16 could be of different shape or construction. No straight section is required if gas velocity from the Nebulizer 12 is suitable. The Curved Section 16b can be of different arc length and radius. The Curved Section 16b could be in coiled form.

The Thermoelectric Plate 22 could be replaced with other means of heating and cooling, such as circulating a temperature controlled liquid through embedded or external passages.

Other means of attaching the Spray Chamber 16 to the Drift Tube 24 are possible.

Since other analytical devices and processes also use nebulization and desolvation as core processes (i.e. mass spectroscopy), the invention could have application other than within an ELSD.

Therefore, the scope of the invention should be determined not by the illustrated embodiment, but by the appended claims and their legal equivalents.

What is claimed is:

1. An aerosol splitting device, comprising
   a. a nebulizer means for generating aerosol particles and
   b. a non-linear spray chamber means for segregating said aerosol particles based upon their momentum, and thus upon their size, and
   c. temperature control of said non-linear spray chamber as means for shifting aerosol size distribution, and
   d. a drain suitably located in said non-linear spray chamber
   whereby said nebulizer propels an aerosol into said non-linear spray chamber and under thermal influence of said temperature control, said aerosol particles shift size distribution either through partial evaporation or condensation, and under geometric influence of said non-linear spray chamber the larger particles are directed to said drain, and the smaller particles are directed to the exit of said non-linear spray chamber.

2. The device of claim 1 wherein the non-linear spray chamber is a stainless steel tube with both a straight section and curved section, said straight section being means for shifting aerosol size distribution, and said curved section providing means for a momentum separator.

3. The device of claim 1 wherein the source of thermal energy for said temperature control is a thermoelectric plate also known as a peltier device, whereby the pettier may raise the temperature of said non-linear spray chamber when operating as a heater, and may decrease the temperature of said non-linear spray chamber when operated as a cooler.

4. The device of claim 3 wherein two aluminum plates of predetermined shape transfer thermal energy between said peltier device and said non-linear spray chamber, the predetermined shape being such that a flat surface exists for intimate thermal contact with said peltier device, a formed recess exists for intimate thermal contact with said non-linear spray chamber, and that the two plates maintain intimate thermal contact with each other when assembled.

* * * * *